(12) United States Patent
Mirho

(10) Patent No.: US 10,350,447 B1
(45) Date of Patent: Jul. 16, 2019

(54) BIOMECHANICAL ARM EXTENSION WITH PROXIMITY DETECTOR

(71) Applicant: FSP LLC, Crescent City, CA (US)

(72) Inventor: Maxwell C Mirho, Lake Oswego, OR (US)

( * ) Notice: Subject to any disclaimer, the term of this patent is extended or adjusted under 35 U.S.C. 154(b) by 238 days.

(21) Appl. No.: 15/616,831

(22) Filed: Jun. 7, 2017

Related U.S. Application Data

(60) Provisional application No. 62/346,985, filed on Jun. 7, 2016.

(51) Int. Cl.
*A63B 21/00* (2006.01)
*A61F 5/01* (2006.01)
*B25J 9/00* (2006.01)
*B25J 9/16* (2006.01)
*G06F 3/01* (2006.01)

(52) U.S. Cl.
CPC .......... *A63B 21/4017* (2015.10); *A61F 5/013* (2013.01); *B25J 9/0006* (2013.01); *B25J 9/1651* (2013.01); *G06F 3/014* (2013.01); *G06F 3/016* (2013.01)

(58) Field of Classification Search
CPC ........................ B25J 9/0006; A63B 21/4017
See application file for complete search history.

(56) References Cited

U.S. PATENT DOCUMENTS

| | | | | |
|---|---|---|---|---|
| 8,425,436 B2* | 4/2013 | Sankai | ................. | A61H 1/0237 318/400.39 |
| 8,800,366 B2* | 8/2014 | Scott | .................... | A61B 5/1038 414/2 |
| 9,327,398 B2* | 5/2016 | Sankai | ................... | B25J 9/0006 |
| 2008/0304935 A1* | 12/2008 | Scott | ................... | A61B 5/1038 414/5 |
| 2010/0063601 A1* | 3/2010 | Sankai | ................. | A61H 1/0237 623/25 |
| 2010/0217163 A1* | 8/2010 | Sankai | .................. | B25J 9/0006 601/5 |

* cited by examiner

*Primary Examiner* — Gerald McClain
(74) *Attorney, Agent, or Firm* — Rowan TELS LLC

(57) ABSTRACT

An elbow harness connected to a forearm harness, the forearm harness supporting a rod driven by a power source, and a proximity detector at a distal end of the forearm harness proximate with where a hand exits the forearm harness when worn. The proximity detector is configured to trigger the power source to drive the rod from a retracted position on the forearm harness to an extended position on the forearm harness.

8 Claims, 4 Drawing Sheets

BIOMECHANICAL ARM EXTENSION WITH PROXIMITY DETECTOR

This application (Ser. No. 15/616,831) claims priority and benefit under 35 U.S.C. 119 to U.S. Application No. 62/346,985, filed on Jun. 7, 2016, which is incorporated herein by reference in its entirety.

BACKGROUND

In recent years, various aiding apparatuses have been developed for aiding and enhancing movements of human limbs. For example, wearable motion assistive devices have been developed with a joint that rotatably couples multiple arms. An actuator rotates one arm relative to another, and a rotation angle of the arm is detected by an angle sensor.

In another example, devices have been developed with a rotation angle detecting apparatus in which a detection element is disposed in a radial direction of a rotating axle. A reflective tape is spirally fixed on a circumferential surface of the rotating axle. Light is projected in a direction intersecting the reflective tape, and reflected light from the reflective tape is captured with the detection element. Based on the amount of displacement in the incident position of the reflected light from the reflective tape as the rotating axle is rotated, the rotation angle of the rotating axle is detected.

In yet another example, a monitoring system has been developed for monitoring an operating status of a motor. In this monitoring system, sensors are used to monitor the operating status of the motor. If data regarding the operating status exceeds a threshold, an alert is displayed. There is an ongoing need for such devices, particularly to enhance human speed and power.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
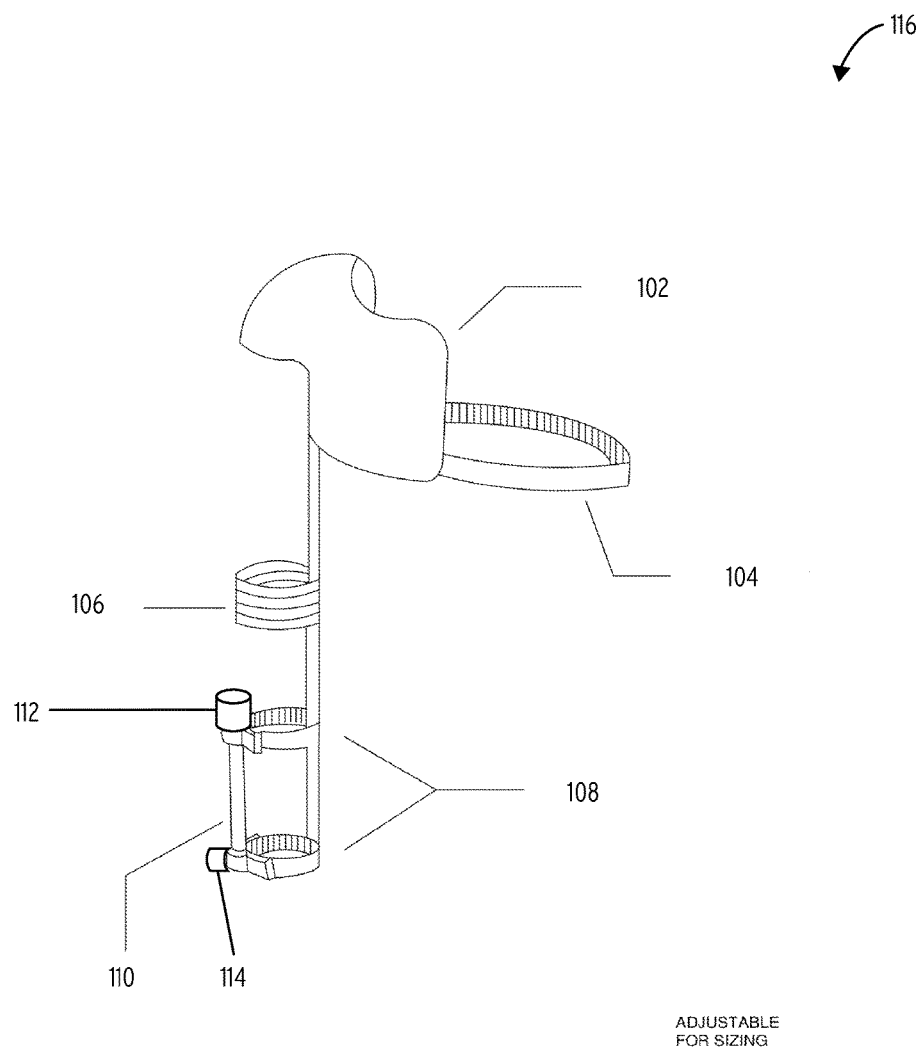
FIG. 1 illustrates the frontal view of a bio-mechanical arm extension 116 in accordance with one embodiment.

FIG. 1 shows a simplified structural diagram of a bio-mechanical arm extension 116, the purpose being to enhance the physical capabilities of the individual wielding it. The wielder thrusts their arm forward and the proximity sensor 114 detects when the wielder's first nears an object (e.g., using IR, LIDAR, or other proximity sensors known in the art) during forward acceleration (e.g., detected via an accelerometer). For enhanced performance, the proximity sensor 114 may be integral with the accelerometer. The proximity sensor 114 signals the power source 112 (e.g., a battery-powered solenoid, or a compressed gas solenoid) to propel the force amplifying rod 202 from the housing barrel 110. These components are secured to the wielder's arm with the forearm straps 108 or equivalent securing mechanisms (e.g., a forearm enclosing support). Due to the powerful force that may be generated, a resistance mechanism is formed by and through the elbow joint 106 (i.e., elbow harness) and chest plate 102. The bio-mechanical arm extension 116 is be secured to the wielder via the elbow joint 106, and the force is conducted through the mechanism to the chest plate 102, which is secured via the shoulder strap 104 (e.g., a shoulder harness). This effectively projects the force of the force amplifying rod 202 through the mechanism without damaging the wielder's body.

The bio-mechanical arm extension 116 may include other, non-illustrated components that would be evident to one of skill in the art in view of this disclosure, such as an integrated circuit controller (e.g., microprocessor or PLC) to receive signals from the various transducers (e.g., the proximity sensor/accelerometer 114) and trigger deployment or retraction of the rod 202.

Figure 2:
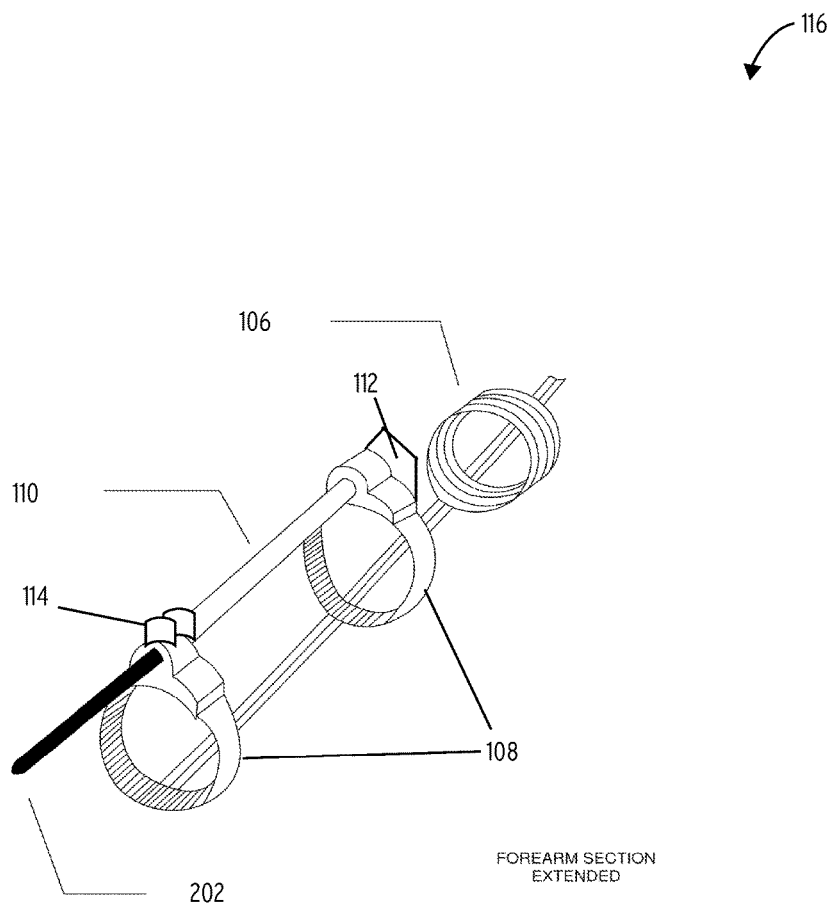
FIG. 2 illustrates a diagonal view of a bio-mechanical arm extension 116 fully extended in accordance with one embodiment.

FIG. 2 shows a diagram of the bio-mechanical arm extension 116 with the force amplifying rod 202 extended from the housing barrel 110. The force amplifying rod 202 and housing barrel 110 are, again, secured to the wielder via the forearm straps 108 and the elbow joint 106. The elbow joint 106 may be selectively flexible so that when a large amount of force is applied to it, the material in the elbow joint 106 hardens (e.g., utilizing an electrorheological or non-Newtonian fluid), further protecting the joint of the wielder. The proximity sensor 114 detects the wielder's first accelerating towards and into proximity with an object and signals the power source 112, which then extends the force amplifying rod 202. The extension of the force amplifying rod 202 may not only increase the amount of power that the wielder can generate, but it may protect the wielder from hitting their own first against the object.

Figure 3:
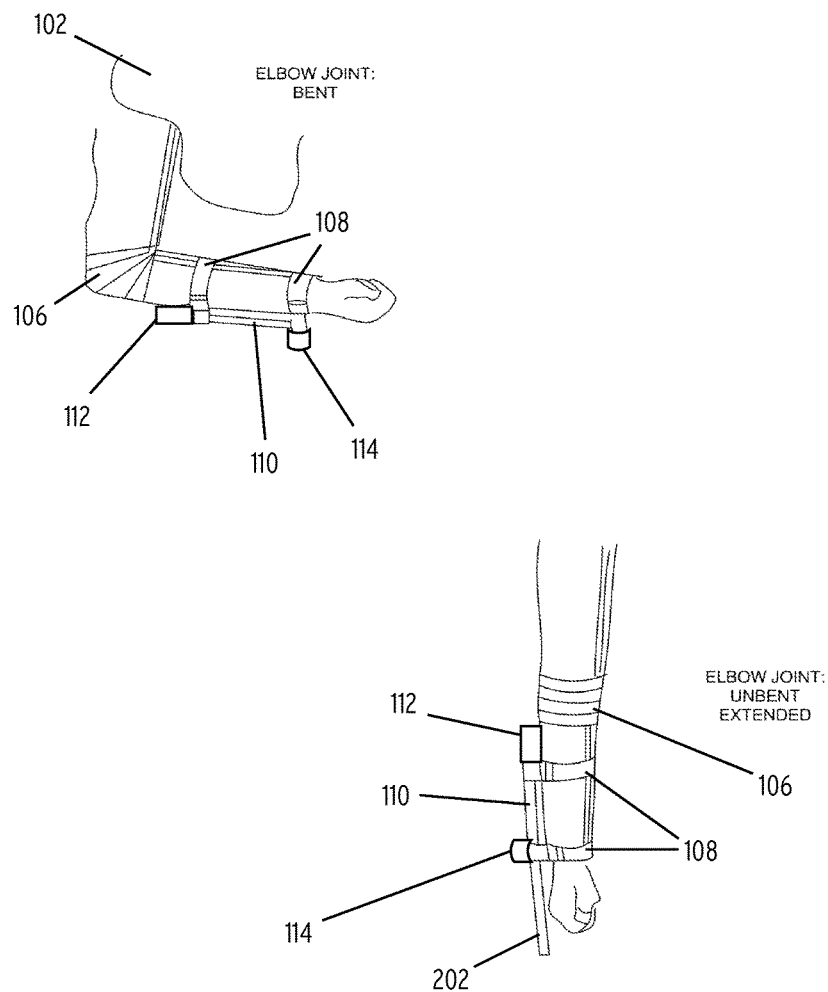
FIG. 3 illustrates two frontal views of a bio-mechanical arm extension 116 and how they may fit on an individual in accordance with one embodiment.

FIG. 3 shows how the bio-mechanical arm extension 116 may fit on the arm and body of the wielder. The forearm straps 108 secure the power source 112 and the force amplifying rod 202 within the housing barrel 110, and the proximity sensor 114 to the forearm. The elbow joint 106 provides more stability and flexibility. The chest plate 102 secures the structure to the body of the wielder.

Figure 4:
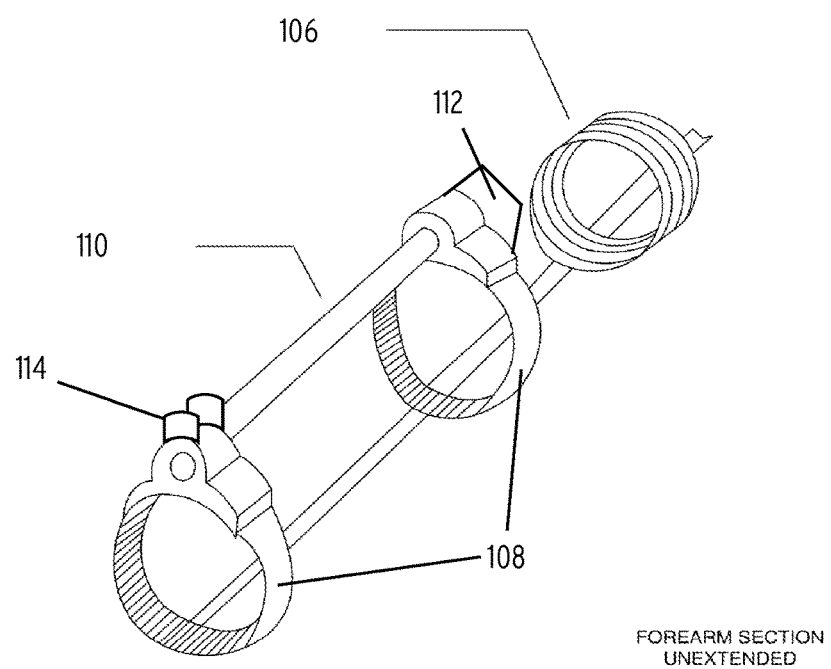
FIG. 4 illustrates diagonal view of a bio-mechanical arm extension 116 without full extension in accordance with one embodiment.

FIG. 4 shows a diagram of the bio-mechanical arm extension 116 with the force amplifying rod 202 retracted from the housing barrel 110. These components are, again, secured to the wielder via the forearm straps 108 and the elbow joint 106. The proximity sensor 114 may detect the wielder's first accelerating towards and becoming proximate with an object (the proximity distance may be configurable in the device logic), signal the power source 112, and extend the force amplifying rod 202, see FIG. 2. When the proximity sensor 114 detects loss of proximity, and/or (in some embodiments) reverse acceleration, e.g., via an accelerometer, and the force amplifying rod 202 is already extended, it signals the power source 112 to retract the force amplifying rod 202 back into the housing barrel 110.

The invention claimed is:
1. An apparatus comprising:
an elbow harness connected to a forearm harness;
the forearm harness supporting a rod driven by a power source;
a proximity detector disposed on a distal end of the forearm harness proximate with where a hand exits the forearm harness when worn; and the proximity detector configured to trigger the power source to drive the rod from a retracted position on the forearm harness to an extended position on the forearm harness.

2. The apparatus of claim 1, further comprising an accelerometer.

3. The apparatus of claim 2, configured such that both an acceleration signal from the accelerometer and a proximity signal from the proximity sensor are needed to trigger the power source to drive the rod into the extended position.

4. The apparatus of claim 1, further comprising a chest plate coupled to receive recoil force from the rod through the elbow harness.

5. The apparatus of claim 1, the proximity sensor configured to trigger the power source to retract the rod from the extended position to the retracted position.

6. The apparatus of claim 5, configured such that both a reverse acceleration signal from the accelerometer and a loss of proximity signal from the proximity sensor are needed to trigger the power source to retract the rod into the retracted position.

7. The apparatus of claim 1, the elbow harness having a flexibility that is variable with the force applied to it.

8. The apparatus of claim 7, the elbow harness comprising one or both of a non-Newtonian fluid and an electrorheological fluid.

* * * * *